April 25, 1961 R. M. WYMAN, JR Plant Pat. 2,052
TAXUS PLANT
Filed May 5, 1960
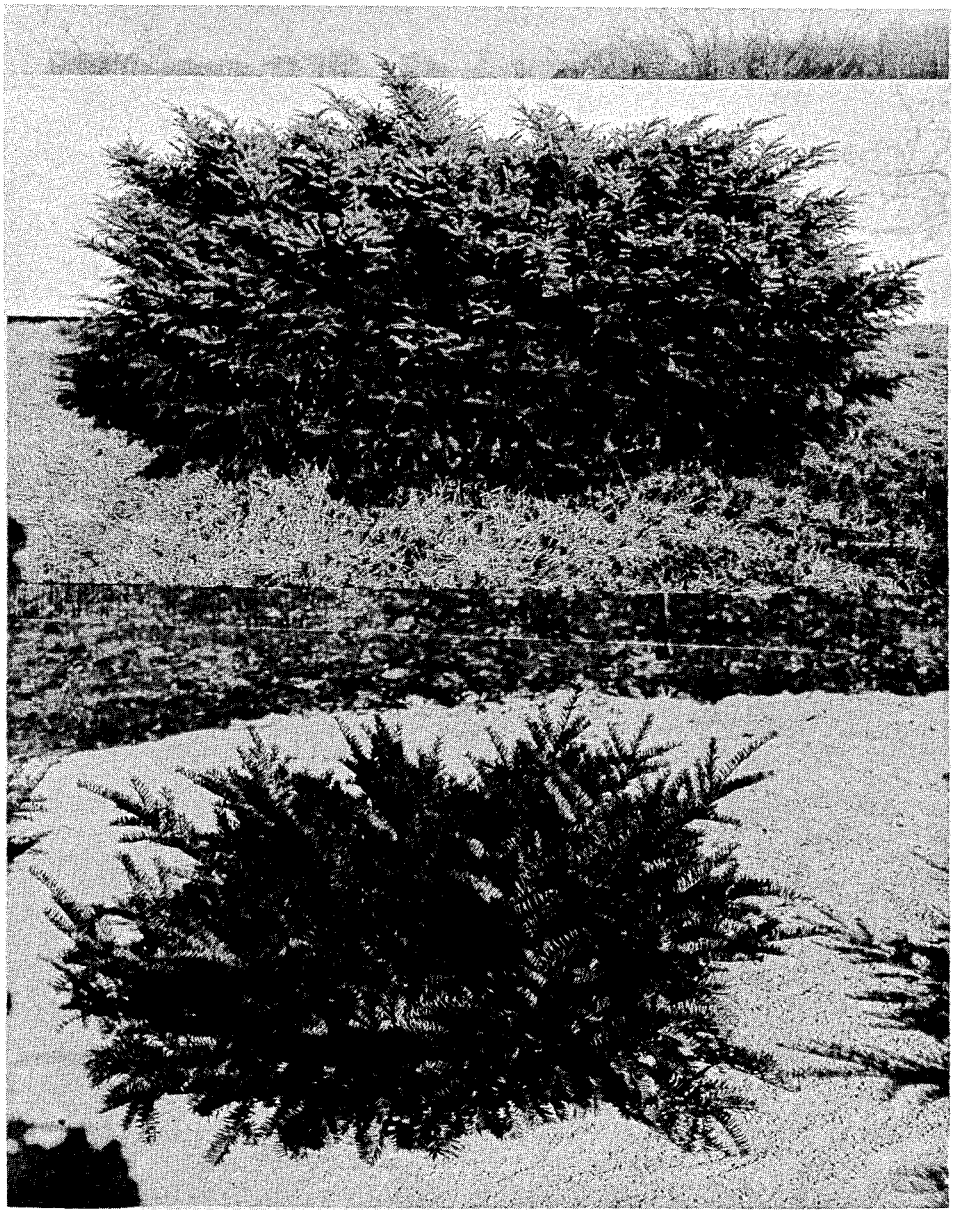
INVENTOR
Richard M. Wyman, Jr.
BY Robb & Robb
ATTORNEYS United States Patent Office Plant Pat. 2,052
Patented Apr. 25, 1961

2,052

TAXUS PLANT

Richard M. Wyman, Jr., Wellesley Hills, Mass., assignor, by mesne assignments, to Wyman's Framingham Nurseries, Inc., Natick, Mass., a corporation of Massachusetts Filed May 5, 1960, Ser. No. 27,232

1 Claim. (Cl. 47—59)

The present invention relates to a new and distinct variety of Taxus plant (commonly known as yew), which was originated by me as a selected, cultivated seedling of *Taxus cuspidata,* the latter having been imported from Japan many years ago.

From the original plants of *Taxus cuspidata,* seeds were harvested and sown on cultivated property owned by my assignee, at Framingham, Massachusetts, and as the seedlings grew under my direction and control as assistant manager of the nursery business of my assignee, I selected and segregated the same according to their non-conforming shapes of more or less spreading form. Of these non-conforming seedlings, my attention was particularly attracted to one plant which was characterized by an unusually low habit of growth, a nearly horizontal branching habit, combined with an unusual fullness in the center of the plant, none of which characteristics are typical of the regular *Taxus cuspidata.* Recognizing the desirability of the unusual form of my new seedling as being particularly applicable for home plantings around low buildings of the so-called ranch or split-level types which have become very popular with the public at the present time, I carefully preserved the new seedling, kept it under close observation, and later asexually reproduced the same, as performed by both winter and summer cuttings at Framingham, Massachusetts, and also near Keller, Accomack County, Virginia. Continued observations of the original seedling and the asexually reproduced plants showed that the aforementioned characteristics were definitely fixed and established, as well as capable of being transmitted through asexual propagation. These observations further showed that the new variety substantially differs in many respects from the usual spreading form of *Taxus cuspidata,* as evidenced by the fact that it has a pronounced flattish oblong-elliptical silhouette, whereas the spreading form of *Taxus cuspidata* has a V-shaped silhouette; it has a well-filled center producing a dense flattish to moderately convexed top, whereas the spreading form of *Taxus cuspidata* has an open empty center; the branches of the new variety spread at only a slight angle above the horizontal, giving a definite horizontal appearance, while the lower branchlets and twigs meet the ground over a broad base, as distinguished from the spreading form of *Taxus cuspidata* in which the main branches rise at a considerable angle from the ground. Unlike *Taxus cuspidata,* the branches of the new variety produce many buds well back on the top side of old wood, which, as they break, grow into small twigs and branchlets which keep the center of the plant well filled. Also unlike *Taxus cuspidata,* all twigs of the new variety, both lateral and terminal, set many buds closely spaced along the sides of the twigs, which, as they break into new growth, develop an ever-increasing overlapping, frond-like branching, thus preventing the development of long loose growths of "blind" wood. The branchlets of the new variety grow in a somewhat recurved manner, arching slightly upward, outward and downward, giving a characteristic drooping appearance to much of the new growth. The plants of the new variety show a remarkably uniform habit of growth when reproduced asexually, with the flat, oblongish outline of the plant being reflected in miniature; the rate of growth of the new variety is less rapid than that of the typical spreading form of *Taxus cuspidata;* and the new variety is winter-hardy, as evidenced by the fact that it has withstood temperatures as low as 30° below zero without injury.

In comparison with the erect form of *Taxus cuspidata* (*capitata*), the new variety substantially differs therefrom by reason of the fact that it develops no central leader.

The outstanding characteristics which distinguish my new variety of Taxus plant from all other varieties, and which represent a unique combination in plants of this type, may be briefly summarized as follows:

(1) Exceptionally uniform, relatively slow-growing, low-growing, nearly horizontal branching, full-centered and dense habits of growth;

(2) A flattish oblong-elliptical silhouette, with a moderately convex top;

(3) The production of lower branchlets and twigs which meet the ground over the entire area and consequently provide a solid, broad base;

(4) A habit of producing many buds on all wood, both old and young, and uniform breaking of the buds into growths of moderate length, producing current growth with many overlapping, frond-like branchlets instead of single shoots.

(5) A somewhat recurving habit of the branchlets which result in moderate arching and drooping appearance of younger growth;

(6) Exceptionally good winter-hardiness; and (7) Relative ease of propagation and absence of "blind" wood.

The accompanying drawing shows views of typical specimens of my new Taxus plant, one of the views illustrating the original discovery plant (which is the larger plant of the two views), and the other view showing a younger asexually reproduced plant as observed from a point nearer the plant to better disclose the details of the branches and foliage.

The following is a detailed description of my new variety of Taxus plant, as based upon observations made from specimens grown at Framingham, Massachusetts, with color nomenclature in accordance with the Nickerson Color Fan, as published by Munsell Color Company, Inc., of Baltimore, Maryland, except where color terms of ordinary dictionary significance are obvious:

Class: Seedling of *Taxus cuspidata.*

Habit: Nearly horizontal branching at the base, with the main stems producing many secondary shoots; young plants have a relatively flat-topped, oblong silhouette; growth ranges from about 4 to 4½ feet wide and about 2 feet tall at the age of about fourteen (14) years, to about 10 to 11 feet wide and about 4 to 4½ feet tall at the age of about thirty-five (35) years, the latter age being the present stage of maturity of the original seedling.

Growth: Moderately slow; uniform; little, if any, shaping or trimming needed.

Branches: All branches are clothed so completely with branchlets that the center of the plant is completely filled; as the plant matures, the normally horizontal branches spread slightly upwards but develop no central leader; branchlets are somewhat recurved, giving a characteristic moderate arching and drooping appearance to new growth.

Leaves: Evergreen; two-ranked; linear, with the *cuspidata* (abruptly pointed) tip typical of the species. Color— substantially the same as in typical *Taxus cuspidata:* upper side—from Moderate Olive Green, Plate 5GY 4/3, darkening toward Grayish Olive Green, Plate 5GY 3/2, but under winter conditions, lightening toward Moderate Olive Green, Plate 2.5GY 4/3; lower side—Strong Yellow Green, Plate 2.5GY 6/8, varying toward moderate Yellow Green, Plate 2.5GY 5/5.

Flowers: Pistillate (female) flowers only are produced; have no ornamental value.

Fruit: Normal red color in the fall, and otherwise normal size and shape corresponding to *Taxus cuspidata*; average abundance.

Hardiness: Very winter-hardy; plants have withstood temperatures as low as 30° below zero without injury.

General observations: The new variety withstands summer light conditions in the southern sections of the United States, as well as in the northern sections, and therefore can be successfully grown throughout a wide range of geographical latitude. It also thrives when grown in soils of many different types and having wide differences in water content.

I claim:

A new and distinct variety of Taxus plant, substantially as herein shown and described, characterized particularly as to novelty by the unique combination of exceptionally uniform, relatively slow-growing, low-growing, nearly horizontally branching, full-centered, and dense habits of growth, a flattish oblong-elliptical silhouette, with a moderately convex top, a habit of producing lower branchlets and twigs which meet the ground over the entire area and providing a solid broad base, a habit of producing many buds on both old and new wood, which buds break with great uniformity, thereby producing current growth of many overlapping frond-like branchlets instead of single shoots, a somewhat recurving habit of the branchlets which gives an arching and drooping appearance to much of the new growth, exceptionally good winter-hardiness, relative ease of propagation, and the absence of "blind" wood.

No references cited.